United States Patent [19]
DeMarinis et al.

[11] Patent Number: 4,849,362
[45] Date of Patent: Jul. 18, 1989

[54] FLUORESCENT INTRACELLULAR CALCIUM INDICATORS

[75] Inventors: Robert M. DeMarinis, Ardmore; Haralambos E. Katerinopoulos, Philadelphia; Katharine A. Muirhead, West Chester, all of Pa.

[73] Assignee: SmithKline Beckman Corporation, Philadelphia, Pa.

[21] Appl. No.: 196,654

[22] Filed: May 19, 1988

[51] Int. Cl.[4] .................. G01N 15/10; G01N 15/12; G01N 21/77; C07D 405/06
[52] U.S. Cl. ........................... 436/63; 436/74; 436/79; 548/181; 548/183; 548/309
[58] Field of Search ............... 548/309, 181, 183; 436/63, 79

[56] References Cited
PUBLICATIONS

*Chemical Abstracts*, 102:200595j (1985) [Grynkiewicz, G., et al.
*J. Biol. Chem.* 1985, 260(6), 3440–50].

*Primary Examiner*—Richard A. Schwartz
*Attorney, Agent, or Firm*—Stuart R. Suter; Janice E. Williams; Alan D. Lourie

[57] ABSTRACT

Invented are new tetracarboxylate compounds which are chelators for calcium ions. Also invented is a useful method of measuring intracellular calcium concentrations using these novel compounds as an optical indicator.

8 Claims, No Drawings

1

FLUORESCENT INTRACELLULAR CALCIUM INDICATORS

This invention relates to tetracarboxy compounds and a method of measuring intracellular calcium using these compounds.

BACKGROUND OF THE INVENTION

Calcium is a key element in the regulation of numerous cellular processes. For example, the development of tension in vascular smooth muscle and cardiac muscle is dependent on a rise in free cystolic $Ca^{++}$ levels. Also, it is known that changes in levels of intracellular $Ca^{++}$ are linked to physiological events as diverse as platelet aggregation exocytosis and cell proliferation.

The role of $Ca^{++}$ in important cellular processes has directed investigation into the development of techniques for measuring calcium ion levels in living cells. The use of optical indicators, in particular tetracarboxylate compounds, appears to be the most reliable method of calcium ion detection. The tetracarboxylate compounds in the form of an ester derivative penetrate the cell membrane and are then enzymatically cleaved in the cell to give tetracarboxylate ions which are impermeable (or permeable only at a slow rate) to the cell membrane. When the tetracarboxylate compounds bind to calcium ion, a shift in the ultraviolet spectrum is produced. This shift is used to measure the amount of bound calcium ion and from a knowledge of the dissociation constants, the intracellular calcium concentration can be determined.

In 1985, the following two tetracarboxylate chelators for calcium detection were reported (Grynkiewicz et al, *J. Biol Chem.* 260:3440) as improved $Ca^{++}$ indicators:

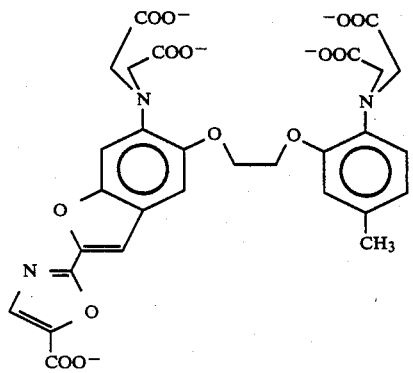

Fura-2

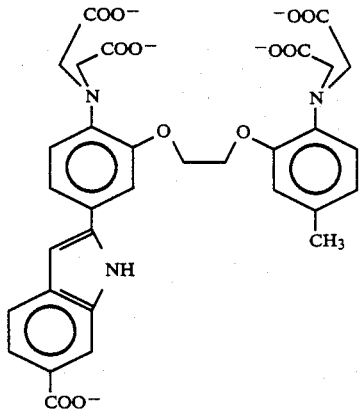

Indo-1

However, the use of Fura-2 and Indo-1 in flow cytometry, which is a very efficient method for measurement of parameters on individual cells (Muirhead, *Trend. Anal. Chem.* 3:107, 1984), is severely limited by their short absorption wavelength which required use of high power lasers with ultraviolet capabilities. The compounds of the present invention have longer absorption wavelength characteristics which make them useful for multiparameter flow cytometric analysis of intracellular calcium ion concentrations in mixed cell populations.

DESCRIPTION OF THE INVENTION

This invention relates to new tetracarboxylate compounds which are useful for measurement of calcium ion concentration in intact cells. In particular, these compounds make intracellular calcium measurements available for a much wider variety of instrumentation and applications than the previously reported tetracarboxylate probes such as Fura-2 and Indo-1. The compounds of this invention are useful for flow cytometric analysis of intracellular calcium ion concentrations.

The compounds of this invention are represented by the following formula:

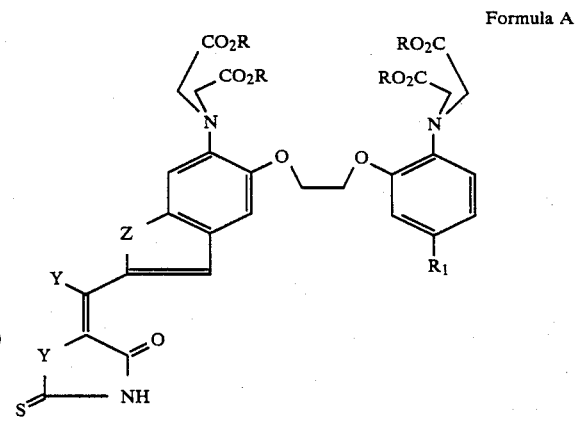

Formula A in which:
R is hydrogen or acetoxymethyl;
$R_1$ is lower alkyl particularly methyl or ethyl;
Z is O, S or NH; and Y is NH or S; or when R is hydrogen, a sodium, potassium or lithium salt thereof.

Compounds of Formula A hereabove in which R is acetoxymethyl are useful in the advantageous flow cytometric method for measurement of cell parameters such as calcium ion concentration. These compounds penetrate the cell membrane and are cleaved enzymatically within the cell. The resulting charged form of the compound chelates calcium.

The compounds of Formula A where R is H or a sodium, potassium or lithium salt thereof may be used as calcium indicators using other techniques such as intracellular microinjection. These compounds are also useful as intermediates to prepare the acetoxymethyl esters of Formula I.

The methods of preparation of compounds of this invention are illustrated by the following reaction schemes and the following examples:

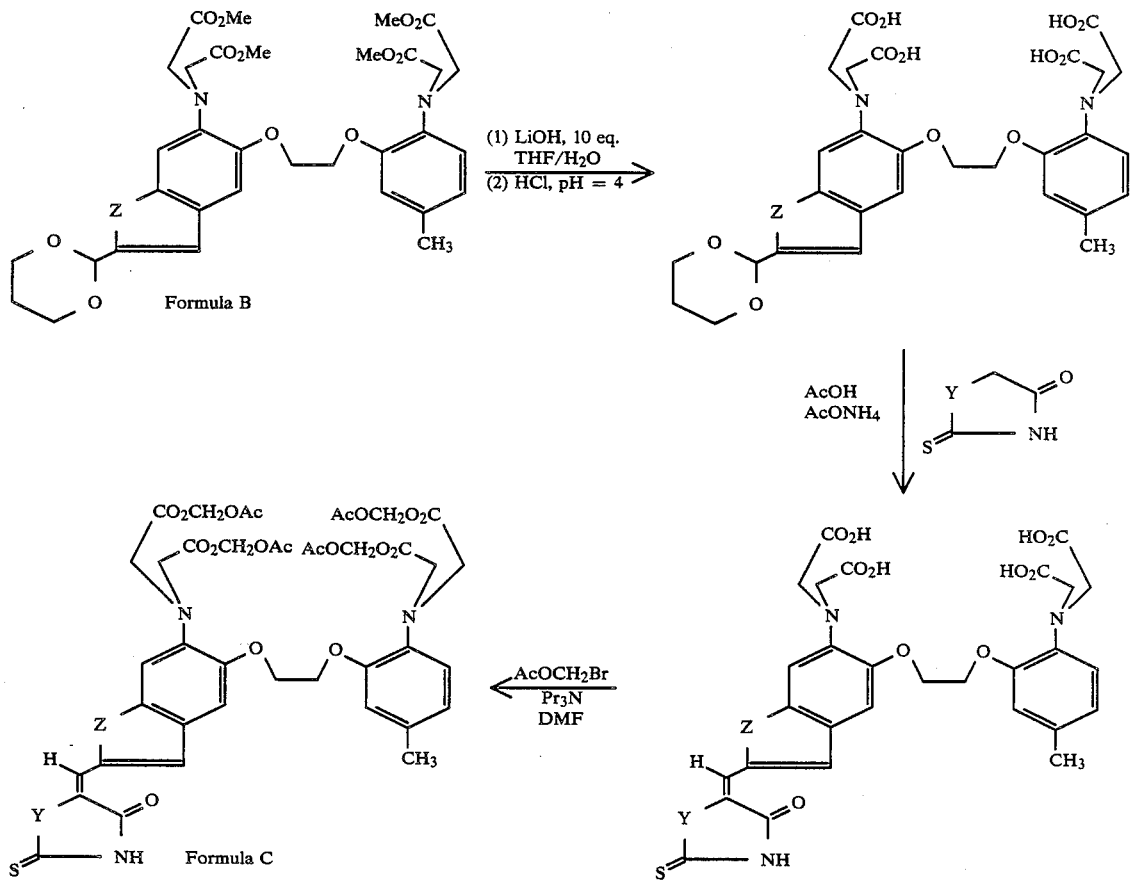

The starting materials in Scheme I are prepared as follows:

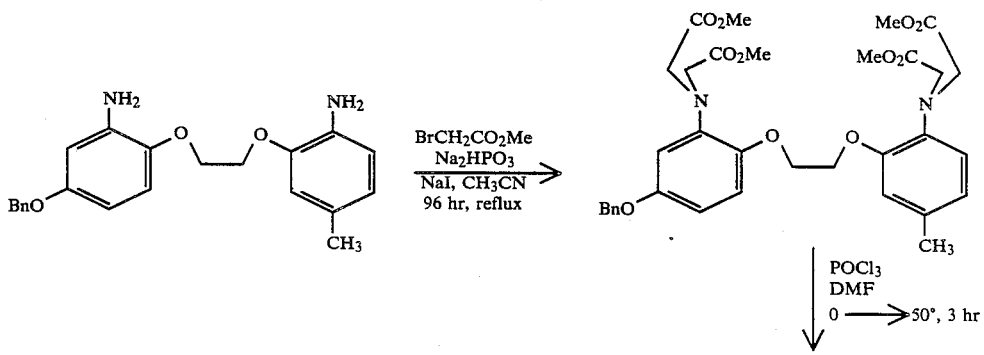

-continued
Scheme II
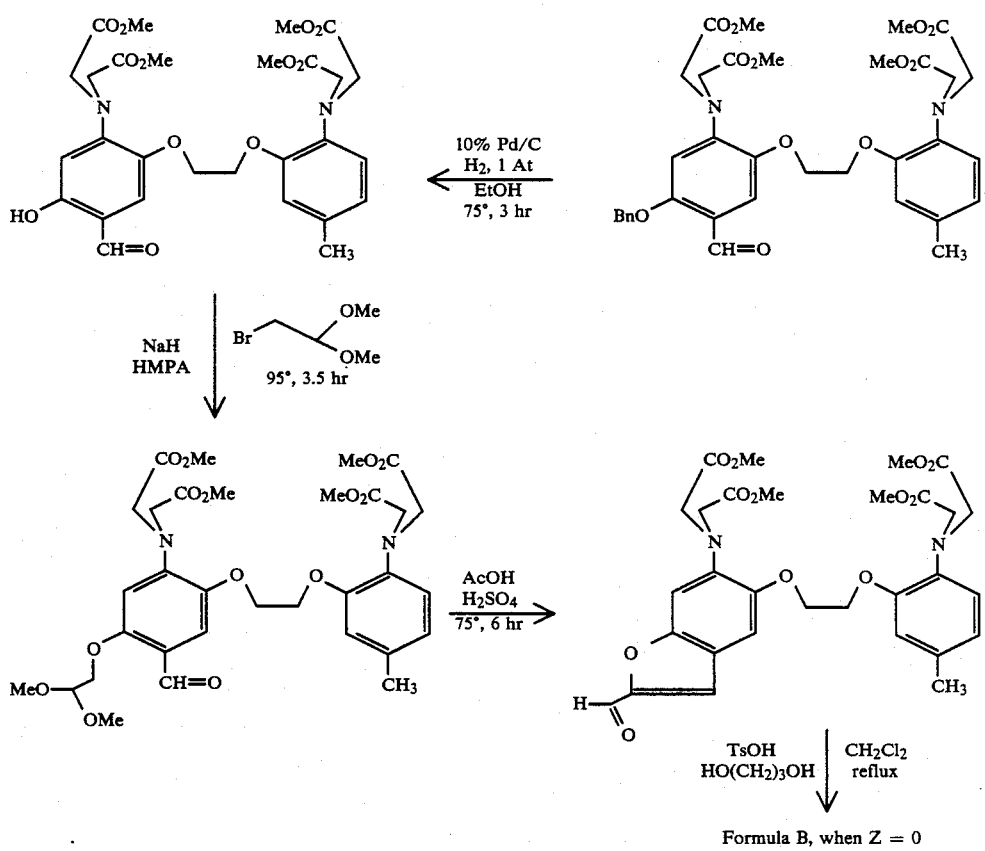
Scheme III
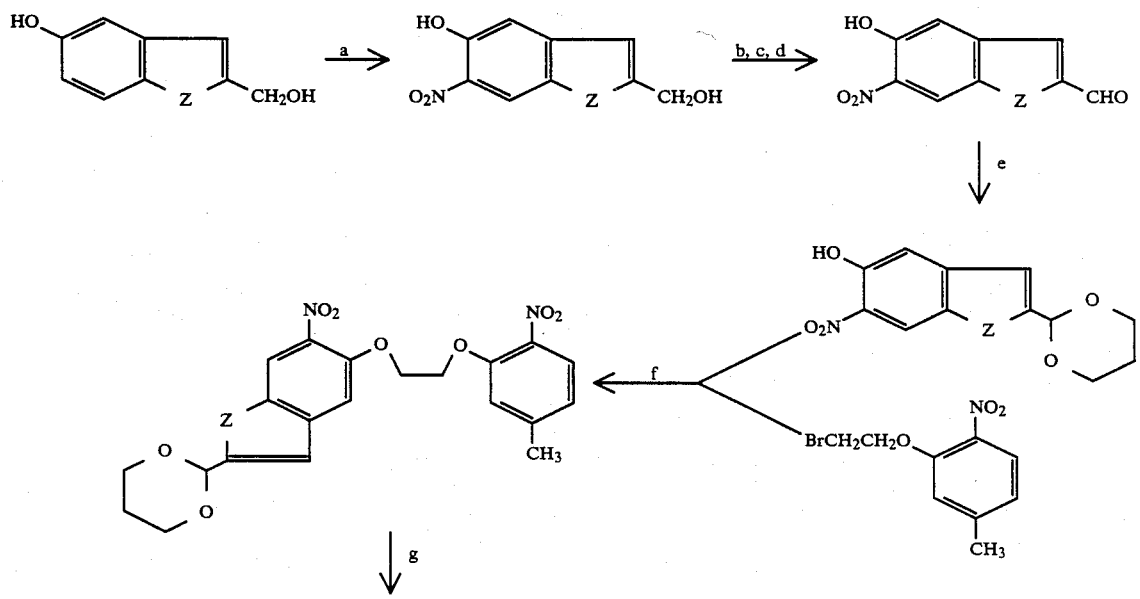

-continued
Scheme III

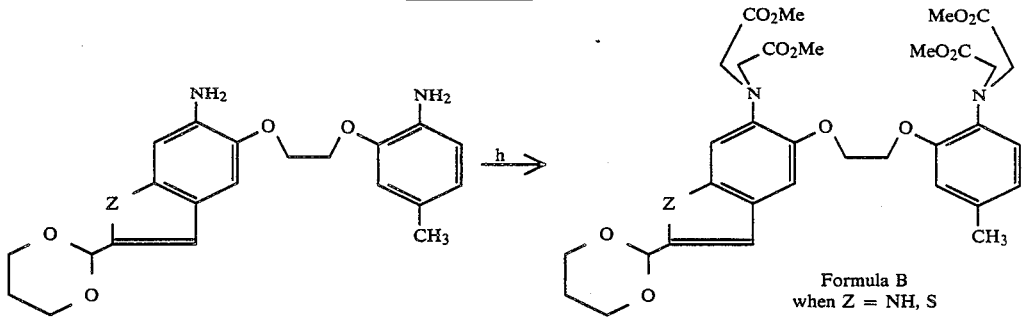

Formula B
when Z = NH, S

LEGEND
a: La(NO$_3$)$_3$, NaNO$_3$, H$_2$O/HCl;
b: TMSCl, K$_2$CO$_3$, DMF;
c: MnO$_2$, CH$_2$Cl$_2$;
d: Bu$_4$N$^+$F$^-$, THF, RT:
e: HO(CH$_2$)$_3$OH, p-CH$_3$C$_6$H$_4$SO$_2$Cl, reflux, 3 hr;
f: K$_2$CO$_3$, DMF, 130° C., 2 hr;
g: 10% Pt/C, H$_2$/1At, EtOH, RT, 10 hr;
h: BrCH$_2$COOMe, Na$_2$HPO$_4$, CH$_3$CN, reflux, 96 hr.

In Schemes I–III, the terms Y and Z, where used, are as defined in Formula A.

According to Scheme I, the ester groups in the starting material (Formula B) are hydrolyzed using, for example, lithium hydroxide and the resulting tetraacetic acid compound is reacted with thiohydantoin or rhodanine to give the 1-[6-amino 2-(5-oxo 2 thioxo-4-imidizoli dinylidene)methyl-5-benzofuranyloxy]-2-(2'-amino-5'-methylphenoxy)ethane-N,N,N',N'-tetraacetic acid and the corresponding 4-thiazolidinylidene compound. Esterifying the carboxylic acid groups using bromomethyl acetate gives the corresponding N,N,N',N'-tetraacetic acid, tetraacetyloxymethyl esters. Similarly, using the 5-benzothienyloxy or the 5-indolyloxy intermediate, the corresponding compounds (Z is S or NH) are prepared.

Schemes II and III relate to the preparation of starting materials for Scheme I.

The following examples are presented to illustrate the invention and are not intended to be limiting. All temperatures are in degrees Centigrade.

EXAMPLE 1

A mixture of 6.23 g (0.017 mol) of 1-(2-amino-4-benzoxylphenoxy)-2-(2'-amino 5'-methylphenoxy)ethane, Grynkiewicz et al, J. Biol. Chem., 260, 3440 (1985) 13.09 g (0.086 mol) methyl bromoacetate, 12.14 g (0.086 mol) dibasic sodium phosphate, and 0.03 g of sodium iodide in 170 ml acetonitrile were heated under reflux for 96 h at which point 1 ml of methyl bromoacetate was added and the system heated for 12 h. Methylene chloride was added to the mixture which was washed with water and NaCl solution, the organic layer was separated, dried over MgSO$_4$, and the solvent was removed in vacuo to yield a brown residue which was treated with hexane ethyl acetate to give 9.7 g, 88% of 1-(2-amino-4-benzoxyphenoxy)-2-(2'-amino-5'-methylphenoxy)ethane-N,N,N',N'-tetraacetic acid tetramethyl ester as yellow crystals mp 95°–97° .IR: 1745; NMR (CDCl$_3$, 250 MHz): 7.43–7.26, m, 5H; 6.79–6.66, m, 4H; 6.50–6.47, m, 2H; 4.98, s, 2H; 4.22, s, 4H; 4.13, s, 4H; 3.58, s, 6H; 3.57, s, 6H; 2.26, s, 3H.

1.18 g (7.70 mmol) of phosphorous oxychloride were added dropwise to 40 ml dimethylformamide (DMF) at 0° in a 20 min period. The solution was stirred at 0° for 0.5 hr, and a solution of 5.02 g (7.70 mmol) of the above prepared tetramethyl ester in 40 ml DMF was added dropwise over a 0.5 hr period. The resulting yellow mixture was heated at 50° for 3 hr, cooled to room temperature, poured onto ice-cold saturated sodium acetate solution, extracted with methylene chloride, and the organic layer was washed with water, NaCl solution, and dried over MgSO$_4$. The solvent was removed in vacuo and the residue was treated with ether to yield 1.12 g, 96% of 1 (2-amino-4-benzoxy-5 -benzaldehyde)oxy-2 (2'-amino 5'-methylphenoxy)ethane N,N,N',N'-tetraacetic acid tetramethyl ester as a light yellow solid, mp 127°–129°.ir: 1740, 1660: nmr(CDCl$_3$, 250 MHz):10.32, s, 1H; 7.40–7.36, m, 5H; 7.29, s, 1H; 6.75, d, 5 Hz, 1H; 6.67, d, 5Hz, 1H; 6.65, s, 1H; 6.30, s, 1H; 5.11, s, 2H; 4.23, br s, 4H; 4.19, s, 4H; 4.11, s, 4H; 3 59, s, 6H; 3.57, s, 6H; 2.26, s, 3H.

The 4-benzoxy group was split to give the corresponding 4-hydroxy compound by the following procedure:

A mixture of 1.1 g (1.60 mmol) of the above prepared benzaldehyde compound and 0.11 g of 10% palladium on charcoal in 20 ml of ethanol was hydrogenated under atmospheric pressure and at 75° (at which temperature the benzaldehyde compound dissolves) for a 3 hr period. The solution was then diluted with methylene chloride, filtered, and the solvents were removed in vacuo to yield 0.98 g (quant.) of the 4-hydroxy compound as a gray powder, mp 130.5°–132.5°. ir:3400 (br), 1740, 1625; nmr (CDCl$_3$, 250 MHz): 11.20, s, 1H, 9.26, s, 1H; 6.91, s, 1H; 6.79–6.66 m, 4H; 6.15, s, 1H; 4.23, s, 8H; 4.12, s, 4H; 3.608, s, 6H; 3.605, s, 6H; 2.23, s, 3H; ms (CI):m/e 591 (M+H)$^+$.

To a suspension of 43.0 mg (2.20 mmol) of sodium hydride in 40 ml of hexamethylphosphoramide cooled at 0°, was added 1.18 g (2.0 mmol) of the above prepared hydroxy compound. The resulting solution was stirred for 5 min, and 0.85 g (5.0 mmol) bromoacetaldehyde dimethyl acetal were added in one portion. The solution was heated at 85°–95° for 3.5 hr, then cooled at room temperature, diluted with methylene chloride, washed five times with NaCl solution, the organic layer was dried over Na$_2$SO$_4$, the solvent was removed and the residue was treated with methylene chloride ether to give 1.12 g, 83% of 1-[2-amino-4-(2,2-dimethoxyethoxy)-5-benzaldehyde]oxy-2-(2'-amino-5'methylphenoxy) ethane N,N,N',N'tetraacetic acid, tetramethyl ester. ir: 1220; nmr (CDCl3, 250 MHz): 10.27, s, 1H; 7.28, s, 1H; 6.76–6.65, m, 3H; 6.30, s, 1H; 4.70, t, 5.1 Hz, 1H, 4 23, s, 8H; 4.11, s, 4H; 4.02, d, 5.1 Hz, 2H; 3.599, s, 6H; 3.585, s, 6H; 3.47, s, 6H; 2.26, s, 3H; ms (CI):679 m/e (M+H)+

To a solution of 0.17 g (0.25 mmol) of the above prepared intermediate in 25 ml glacial acetic acid was added 0.028 ml (0.50 mmol) of 96% H2SO4 and the system was stirred at room temperature for 24 hr. The solution was then diluted with water and extracted repeatedly with chloroform; the organic layers were dried over Na2S04 and the solvent was removed in vacuo. The orange residue was treated with glacial acetic acid at 75° for 6 h. The pure product 1-(6-amino 2-benzofuraldehyde-5-oxy)-2-(2'-amino-5'-methylphenoxy)ethane N,N,N',N' tetraacetic acid, tetramethyl ester (0.09 g, 59%, mp 146°-147°) was isolated as described above. ir: 1748, 1680; nmr (CDCl3, 50MHz): 9.72, s, 1H; 7.44, s, 1H; 7.10, s, 1H; 6.95, s, 1H; 6.75-6.67, m, 3H; 4 30, s, 2H; 4.29, s, 2H; 4.23, s, 4H; 4.12, s, 4H; 3.59, s, 6H; 3.56, s, 6H: 2.27, s, 3H; ms (CI):m/e 615 (M+H)+.

To a solution of 0.22 g (0.33 mmol) of the above prepared benzofuraldehyde intermediate in 10 ml methylene chloride, was added 0.03 g (0.36 mmol) of 1,3 propanediol, followed by 0.6 mg p-toluenesulfonic acid. The solution was heated under reflux for 3 hours, stirred overnight at room temperature, diluted with methylene chloride, washed with water and NaCl solution. The organic layer was dried over Na2SO4, and the solvent was removed in vacuo to yield a yellow residue which was purified by flash chromatography using 20% petroleum ether in ether as eluent to give the 2-propylenedioxybenzofuranoxy intermediate. The product yield was 180 mg, 81%, mp 147°-148° .ir:1165, nmr (CDCl3, 250 MHz): 701, s, 1H; 6.99, s, 1H; 6.79-6.60, m, 4H, 5.66, s, 1H; 4.28, br s, 4H; 4.17, s, 4H; 4.12, s, 4H; 4.06-3.93, m, 4H; 3.56, s, 6H; 3.53, s, 6H; 2.26, s, 3H; 1.57-1.40, m, 2H; ms (CI): 673 m/e (M+H)+.

The ester groups of the above prepared intermediate were hydrolyzed as follows. The intermediate, 0.22 g (0.32 mmol), was dissolved in 4 ml THF. To this solution was added 0.134 g (3.2 mmol) lithium hydroxide monohydrate dissolved in 4 ml water and the solution was stirred at room temperature overnight. Dilute HCl solution was added to adjust the pH to 4–5, and the resulting oil was extracted with methylene chloride, washed with water and NaCl solution, dried over Na2SO4, and the solvent was removed in vacuo to yield 0.196 , 99% of the N,N,N',N'-tetracetic acid 2-propylenedioxybenzofuranoxy intermediate, mp 110°-111° (d). ir:3400-2540; nmr (CDCl3, 250 MHz): 7.18, s, 1H; 6.96, s, 1 H; 6.80, s, 1H; 6.71, s, 1H; 6.66, s, 2H; 5.67, s, 1H; 4.27, br s, 4H; 4.10, s, 4H; 4.01 s, 4H; 2.22, s, 3H; ms (FAB) m/e 617 (M+H)+.

A mixture of 0.05 g (0.08 mmol) of the above prepared intermediate, 0.01 g (0.09 mmol) thiohydantoin and 0.02 g (0.29 mmol) ammonium acetate in 5 ml glacial acetic acid was heated to 75° at which temperature all solid components dissolved. After 1.5 hours stirring at this temperature, an orange red precipitate was formed. This precipitate was treated with ether to yield 0.035 g, 67%, of 1-[6-amino-2-(5-oxo-2-thioxo-4-imidazo lidinylidene) methyl 5 benzofuranyloxy]2 (2'amino 5'-methyl phenoxy) ethane N,N,N',N'-tetraacetic acid as an orange powder mp 164.5°-167° . ir:3600-2500,1726,1490,1192; nmr (DMSO-d6, 250 MHz): 12.0, m, 2H; 7.36, s, 1H; 7.23, s, 1H; 7.18, s, 1H; 7.05, s, 1H; 6.80, s, 1H; 6.65, s, 2H; 6.49, s, 1H; 4.29, s, 4H; 4.13, s, 4H; 3.99, s, 4H; 2.22, s, 3H; ms (FAB) m/e 657 (M+H)+.

Potassium carbonate, 0.002 g (0.015 mmol) was added to a solution of 2.0 mg (0.003 mmol) of the above prepared tetracarboxylic acid compound in 2 ml dry DMF. The mixture was stirred at room temperature for 0.5 hr, 0.001 ml (0.006 mmol) tripropylamine was added in one portion, and the system was stirred for 0.5 hr. Bromomethyl acetate, 45.0 mg (0.03 mmol), was added and after 5 min stirring, thin layer chromatography (silica 25% methanol in methylene chloride) indicated that all starting material was consumed and a less polar component was formed. The solvent was removed in vacuo and the residual solid was treated with water and then with ether to give 2 mg of 1-[6-amino-2-(5-oxo-2-thioxo-4-imidazolidinyl-idene) methyl-5-benzofuranyloxy]-2-(2'-amino-5'-methyphenoxy)ethane N,N,N',N'-tetraacetic acid, tetraacetyloxymethyl ester. nmr (DMSO-d6, 250 MHz):7.50–6.57,m, 7H; 5.60, s, 4H; 5.59, s, 4H; 4.28, br s, 4H; 4.14, s, 4H; 2.21, s, 2H; 2.00, s, 12H; ms (FAB) m/e 945 (M+H)+.

EXAMPLE 2

By the procedure of Example 1, using rhodanine in place of thiohydantoin, the following compounds are prepared:
1-[6-amino-2-(5-oxo-2-thioxo-4-thiazolidinylidene) methyl-5-benzofuranyloxy]-2-(2'-amino-5'-methylphenoxy) ethane N,N,N',N'-tetraacetic acid and the tetra acetyloxymethyl ester thereof.

EXAMPLE 3

2-hydroxymethyl-5-hydroxyindole is treated with lanthanum trinitrate, sodium nitrate and aqueous hydrochloric acid to give the 5-nitro derivative. The 2-hydroxymethyl group is oxidized by protecting the 5-hydroxy group using trimethylsilyl chloride, treating with manganese oxide in dichloromethane, then treating with tetrabutylammonium fluoride in tetrahydrofuran at room temperature to give 4-hydroxy-5-nitro-2-indolealdehyde.

The above prepared aldehyde is reacted with 1,3-propanediol by the procedure described in Example 1 to give the 2-propylenedioxyindole intermediate.

A mixture of the above prepared propylenedioxy compound, 3-bromoethoxy-4-nitrotoluene, and potassium carbonate in dimethylformamide is heated at 130° for 2 hours. The product is 1-(6-nitro-2-propylenedioxy-5-indolyloxy)-2-(2'-amino-5'-methylphenoxy)ethane.

The nitro groups in the above prepared intermediate are reduced to amino groups by hydrogenating at room temperature for 10 hours in ethanol using platinum on charcoal.

Treating the diamino intermediate with methyl bromoacetate and dibasic sodium phosphate in acetonitrile and refluxing for 96 hours gives the N,N,N',N'-tetraacetic acid tetramethyl ester (Formula B where Z is NH).

By the procedures of Example 1, the ester groups are hydrolyzed to acid groups and the resulting intermediate is reacted with thiohydantoin to give 1-[6-amino-2-(5-oxo-2-thioxo-4-imidazolidinyliene) methyl-5- indolyloxy]-2-(2'-amino-5'-methylphenoxy)ethane N,N,N',N'-tetraacetic acid.

The corresponding tetraacetyloxymethyl ester is prepared by reacting the above prepared tetraacetic acid with bromomethyl acetate by the procedure of Example 1.

EXAMPLE 4

By the procedure of Example 4, using 2-hydroxymethyl-5-hydroxybenzothiophene in place of the corresponding indole, the following are prepared:

1-[6-amino-2-(5-oxo-2-thioxo-4-imidazolidinylidene)methy-5-benzothienyloxy]-2-(2'-amino-5'-methylphenoxy)ethane N,N,N',N'-tetraacetic acid and the tetraacetyloxymethyl ester.

The following procedures illustrate the utility of the tetracarboxylate compounds of this invention for measurement of intracellular calcium levels in two different cell types and measurement systems.

Flow cytometric measurement of lymphocyte subset responses to calcium ionophore

Human peripheral blood mononuclear cells are purified by density gradient separation. Cells ($4 \times 10^6$/ml) are loaded with a tetracarboxylate compound of this invention by incubation for 45 minutes at 37° C. in RPMI 1640 medium containing 25 mM HEPES buffer (pH 7.3-7.4), 2% autologous serum, and 0.5-2.5 $\mu$M of the tetarcarboxylate compound. The ester groups are cleaved by intracellular esterases (for example as described in ,L Tsien, RY, Nature 290:527 528, 1981), trapping the charged form of indicator whose free carboxyl groups chelate calcium. After loading, cells are washed 3 times with RPMI-HEPES-2% serum medium and divided into two portions. One portion is held at $4 \times 10^6$/ml and room temperature in medium until flow cytometric analysis is performed (1-2.5 hours post loading). The other portion is labeled with fluorescein- labeled anti-Leu2a, anti Leu3a, anti LeuIIa, and/or anti HLA DR antibodies recognizing specific lymphocyte subtypes (Becton Dickinson Immunocytometry Systems) by incubation with the manufacturer's recommended concentration for 15 minutes at 4° C. in RPMI HEPES 2% serum. After antibody labeling, the cells are washed 3 times and held at $4 \times 10^6$/ml at room temperature in the same medium until flow cytometric analysis is carried out. Cell viabilities at the time of analysis are assessed by ability to exclude propidium iodide.

Flow cytometric analysis is performed on a Coulter EPICS 753 with an argon ion laser providing excitation of 200 mW @488 nm. Right angle scatter is collected using a 488 nm longpass dichroic mirror and a 488 nm bandpass filter. Forward and right angle scattered exciting light are used to distinguish lymphocytes from monocytes, and fluorescence histograms are collected gated on the characteristic lymphocyte scatter region. "Antibody" (fluorescein) fluorescence is collected using a 560 nm shortpass dichroic mirror and 525 nm bandpass plus 515 nm longpass filter. "Calcium" fluorescence is collected using a 620 nm shortpass dichroic mirror and 665 nm longpass filter. Because the free (non calcium bound) form is preferentially excited by 488 nm light, the signal intensity at wavelengths greater than 665 nm should be inversely related to the level of intracellular calcium.

For flow cytometric analysis, 100 $\mu$l cells at room temperature in medium are admixed with 400 $\mu$l 37° C. medium and fluorescence versus time accumulated for 5 minutes at 37° C. with or without addition of 10 $\mu$M ionomycin, 2 $\mu$g/ml phytohemagglutinin, 10 $\mu$g/ml anti-human immunglobulin, or other suitable stimulus. Elevation of intracellular calcium by treatment with stimulus produces a decrease in fluorescence intensity and the responses of individual lymphocyte subsets can be determined using a single visible wavelength laser line for excitation. To carry out similar determinations by flow cytometry using Indo 1 typically uses 5-10 fold higher loading concentrations of indicator dye and requires two separate lasers, one of which must have uv capability (Rabinovitch et al., J. Immunol. 137:952–961, 1986).

Quantitative microscopic measurement of response to vasopressin stimulation in individual A10 smooth muscle cells A10 smooth muscle cell cultures are plated on coverslips and examined in the log phase of growth. Cells are loaded with an indicator dye (Indo-1 or a tetracarboxylate compound of this invention) by incubation in pH 7.2 Dulbecco's phosphate buffered saline containing $Ca^{2+}$ and $Mg^{2+}$, 5 mM glucose, 15 mM HEPES, 0.1% bovine serum albumin and 5 $\mu$M dye for 30 minutes at 37° C. After loading, cells are washed 3 times and held at room temperature in the same buffered salt solution until microscopic analysis is performed.

Analysis is carried out using a Meridian ACAS 470 equipped with a 5 W argon ion laser and dual photomultipier tubes for fluorescence quantitation. Laser output of 100 mW at 356–365 nm is used to excite the fluorescence of calcium bound Indo-1, which is collected using a 405 nm bandpass filter. Laser output of 100 mW at 488 nm is used to excite the fluorescence of calcium-free tetracarboxylate, which is collected using a 640 nm longpass filter. All analyses are carried out at room temperature. A single cell is centered in the microscope objective and then repetitively scanned (3 sec/scan) for 1 minute to establish baseline fluorescence level. At 1 minute, the glucose salt solution is rapidly withdrawn via syringe and replaced with an equal volume of solution containing 100 nM vasopressin. Vasopressin is known to stimulate release of calcium from internal stores and uptake of calcium from the external medium in this cell type. Repetitive scanning is continued for approximately 2 minutes post stimulation.

The vasopressin stimulated increase in intracellular calcium causes a decrease in the calcium free form of the tetracarboxylate and therefore a decrease in its 488nm excited fluorescence. Conversely, it caused an increase in the calcium bound form of Indo 1 and an increase in its 356–365nm excited fluorescence. Both indicators give a similar assessment of the magnitude and time course of the response. However, Indo-1 could not be used in a system without uv laser capability while the tetracarboxylate could. Indo 1 also could not be used to clone cells exhibiting (or lacking) a calcium response, due to the uv absorbing properties of dishes used for cloning. However, a tetracarboxylate of this invention is suitable for use in cloning studies.

What is claimed is:

1. A compound of the formula:

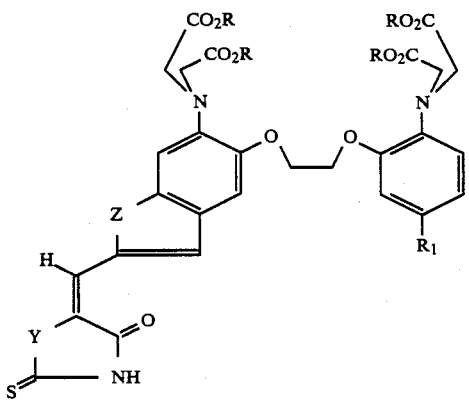

in which:

R is hydrogen or acetoxymethyl;

$R_1$ is methyl or ethyl;

Z is O, S or NH: and

Y is NH or S; or when R is hydrogen, a sodium, potassium or lithium salt thereof.

2. A compound according to claim 1 in which R is acetoxymethyl.

3. A compound according to claim 1 in which $R_1$ is methyl.

4. A compound according to claim 1 in which $R_1$ is methyl, Z is O and Y is NH.

5. A compound according to claim 2 in which $R_1$ is methyl.

6. A compound according to claim 2 in which $R_1$ is methyl, Z is O and Y is NH.

7. A method of determining intracellar calcium concentration in intact cells via an optical measurement system which comprises treating said cells with a sufficient quantity of a compound of claim 1 to act as an optical indicator.

8. A method of claim 7 in which flow cytometry or quantitative fluorescence microscopy is used to measure intracellular calcium concentrations.

* * * * *